US011911092B2

(12) United States Patent
Brockmann et al.

(10) Patent No.: US 11,911,092 B2
(45) Date of Patent: Feb. 27, 2024

(54) ELECTRODE INSTRUMENT AND RESECTOSCOPE, PROTECTED AGAINST SHORT CIRCUIT

(71) Applicant: OLYMPUS WINTER & IBE GMBH, Hamburg (DE)

(72) Inventors: Christian Brockmann, Hollenstedt (DE); Christoph Knopf, Lübeck (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 501 days.

(21) Appl. No.: 16/944,947

(22) Filed: Jul. 31, 2020

(65) Prior Publication Data
US 2021/0045800 A1 Feb. 18, 2021

(30) Foreign Application Priority Data
Aug. 12, 2019 (DE) ...................... 10 2019 121 674.5

(51) Int. Cl.
*A61B 18/14* (2006.01)
*A61B 18/12* (2006.01)
*A61B 18/00* (2006.01)

(52) U.S. Cl.
CPC ........ *A61B 18/149* (2013.01); *A61B 18/1206* (2013.01); *A61B 2018/00083* (2013.01); *A61B 2018/126* (2013.01)

(58) Field of Classification Search
CPC ............ A61B 18/149; A61B 2018/126; A61B 18/1206; A61B 2018/00083
See application file for complete search history.

(56) References Cited

U.S. PATENT DOCUMENTS

| 5,827,274 A | 10/1998 | Bonnet et al. |
| 5,976,129 A * | 11/1999 | Desai ................. A61B 18/1477 606/42 |
| 7,645,286 B2 | 1/2010 | Catanese, III et al. |
| 2001/0053908 A1 | 12/2001 | Brommersma et al. |
| 2003/0130655 A1 * | 7/2003 | Woloszko .......... A61B 18/1482 606/45 |
| 2014/0236143 A1 * | 8/2014 | Ward ................. A61B 18/1442 606/39 |

(Continued)

FOREIGN PATENT DOCUMENTS

| DE | 10028850 C1 | 10/2001 |
| DE | 10 2014 212 102 A1 | 12/2014 |

(Continued)

*Primary Examiner* — Sean W Collins
(74) *Attorney, Agent, or Firm* — Oliff PLC (57) ABSTRACT

A bipolar electrode instrument for use in a resectoscope and having an elongated shaft section, through which a first conductor extends, which forms a working electrode to which high-frequency current can be applied at the distal end of the electrode instrument, and a second conductor further extending through the shaft section, which forms a counter electrode in the distal end region of the electrode instrument. The working electrode and the counter electrode are spatially separated from one another in such a way that the distance between them cannot be bridged by a straight conductor which has a length of 6 mm or less. When used in a resectoscope for endoscopic surgery with a cladding tube, the electrode instrument is mounted so as to be longitudinally displaceable inside the cladding tube.

11 Claims, 3 Drawing Sheets

(56) References Cited

U.S. PATENT DOCUMENTS

| | | | | |
|---|---|---|---|---|
| 2014/0276757 A1* | 9/2014 | Ellman | .............. | A61B 18/1402 |
| | | | | 606/33 |
| 2014/0378965 A1* | 12/2014 | Atwell | ................. | A61B 18/149 |
| | | | | 606/41 |
| 2015/0196350 A1* | 7/2015 | Carmel | ................ | A61B 18/148 |
| | | | | 606/41 |
| 2019/0021786 A1 | 1/2019 | Ward | | |
| 2020/0397500 A1* | 12/2020 | Woloszko | ............ | A61B 18/148 |

FOREIGN PATENT DOCUMENTS

| | | | |
|---|---|---|---|
| DE | 102014212102 | A1 | 12/2014 |
| EP | 2 164 427 | A1 | 3/2010 |
| EP | 2164427 | A1 | 3/2010 |
| EP | 2767250 | A1 | 8/2014 |

* cited by examiner

Fig. 7

ELECTRODE INSTRUMENT AND RESECTOSCOPE, PROTECTED AGAINST SHORT CIRCUIT

BACKGROUND

The invention relates to electrode instruments for use in a resectoscope of the type mentioned in the preamble of claim 1 and a resectoscope of the type mentioned in the preamble of claim 10.

Electrode instruments and resectoscopes of the generic type are used primarily in urology for electrosurgical work in the bladder and urethra. They are usually used for resection and vaporization of tissue, for example tissue in the lower urinary tract. For this purpose, the resectoscopes comprise a generic electrode instrument which is mounted so as to be longitudinally displaceable inside the resectoscope shaft and, after the resectoscope has been inserted, its distal working end can be pushed out of the distal end of the shaft. At its distal working end, the electrode instrument includes an electrosurgical electrode, for example in the form of a loop or vaporization button (e.g., a PlasmaButton). Such instruments are, for example, the OES PRO resectoscopes (Olympus) or other resectoscopes with continuous irrigation according to Iglesias.

The prostate or parts of the prostate can be resected by means of these electrode instruments, for example in the presence of benign prostatic hyperplasia (BPH), i.e., an excessive growth of prostate cells. Such enlargement of the prostate is promoted in the course of a normal aging process by a drop in the level of androgen and an increase in the level of estrogen in the blood. More recently, prostate tissue has been compressed using implants as an alternative to tissue resection. The compression was achieved by implants, which are configured like an anchor at both ends and are able to keep the prostate tissue compressed (UroLift® system). The compression of the tissue reduces the pressure on the urethra at least temporarily so that urine can drain off. A corresponding system is described, for example, in EP 2 164 427 and U.S. Pat. No. 7,645,286 B2.

However, it has been shown that even after such compressive interventions, resection surgery on the prostate tissue may be necessary at a later time due to continuous tissue growth. If these surgeries are carried out with conventional bipolar electrode instruments, there is a risk of damaging the resectoscope if the conductive implants bridge the isolating distance between the working electrode and the shaft, fork tube or optics. With particularly thin electrodes, such as loop electrodes, there is an additional risk that the wire will melt and tear due to a locally increased current density when it comes into contact with the implant.

There is therefore a need for electrode instruments for which the risk of damage to the instrument during surgery on prostate tissue that receives implants is reduced.

DESCRIPTION

This object is achieved by a bipolar electrode instrument with the features of claim 1 and a resectoscope with the features of claim 10. According to the invention, provision is made in particular for the working electrode and counter electrode to be spaced apart from one another or to be arranged such that the distance between them cannot be bridged by means of a conductor which has a length of 6 mm or less. This length corresponds to the length of end or anchor pieces of the above-mentioned prostate implants currently used.

In a first aspect, the invention relates to a bipolar electrode instrument for use in a resectoscope, the electrode instrument having an elongated shaft section through which a first conductor extends, which forms a working electrode to which high-frequency current can be applied at the distal end of the electrode instrument, wherein a second conductor extends through the shaft section, which second conductor forms a counter electrode in the distal end region of the electrode instrument, characterized in that the working electrode and the counter electrode are spatially separated from one another in such a way that the distance between them cannot be bridged by means of a straight conductor, which has a length of 6 mm or less.

In a second, related aspect, the invention relates to a resectoscope for endoscopic surgery having a cladding tube, characterized in that an electrode instrument according to the invention is mounted so as to be longitudinally displaceable inside the cladding tube.

The resectoscope according to the invention is suitable for various interventions in endoscopic surgery, in particular in electrosurgical surgery. For example, the resectoscope can be used for prostate resection. At the same time, the resectoscope can also be used for a variety of other operations, such as bladder resections.

In a conventional embodiment, the resectoscope according to the invention has a tubular shaft. The resectoscope shaft comprises an elongate cladding tube. In addition to the shaft, the resectoscope includes a handle system for holding and operating the resectoscope, which handle system usually consists of two handle parts.

The bipolar electrode instrument according to the invention is used as a passage instrument in such a resectoscope. For this purpose, the electrode instrument is mounted in the resectoscope so as to be longitudinally displaceable, preferably inside the cladding tube of the resectoscope. The electrode instrument can be arranged outside an inner tube running in the cladding tube, i.e., between the cladding tube and the inner tube, or inside the inner tube. In addition to the electrode instrument, further passage instruments can be arranged in the shaft of the resectoscope. The resectoscope usually additionally comprises, for example, rod-shaped optics, an illuminant and/or an irrigation system.

The electrode instrument has, in a conventional embodiment, an elongated shaft section which, as described above, is arranged so as to be longitudinally displaceable and optionally rotatable about its longitudinal axis in the interior of the resectoscope shaft. The proximal end of the shaft section is functionally connected to a carriage of the resectoscope transporter which can be actuated by means of the handle. At the distal end of the electrode instrument, a working electrode to which high-frequency current can be applied is formed.

The electrode instrument can, in particular in the shaft section, have one or two support arms on or between which the working electrode and the counter electrode can be held. For example, the working electrode can be securely held between the distal ends of two support arms or at the distal end of one support arm. The working electrode is preferably arranged so that the view of the point of surgery is not significantly impaired.

Two conductors extend through the support arm or shaft section. At the distal end of the electrode instrument, the first conductor forms a working electrode (also: active electrode) to which high-frequency current can be applied. The second conductor forms a counter electrode (also: neutral electrode) in the distal end region of the electrode instrument. The working electrode is thus electrically conductively connected to the first conductor and the counter electrode to the second conductor. In contrast, the electrodes are not connected to one another or to the other conductor in an electrically conductive manner. In this way, the current flows through the electrically conductive tissue and/or the liquid that is located between the two electrodes during a surgical intervention between the two electrodes. According to the invention, the electrode instrument is thus a bipolar electrode instrument. The advantages of bipolar over monopolar instruments are well known to those skilled in the art. The two conductors are usually connected to two poles of a high-frequency generator via connection cables.

Both conductors are electrically conductive and can for example be configured as a conductor wire. In the shaft section, with the exception of the electrodes, the conductor wire can, e.g., be electrically isolated from the resectoscope shaft. For this purpose, the support arm or arms can generally have an insulating sleeve surrounding the conductor in question, i.e., an electrically insulating sleeve. The insulating sleeve can have a hollow cylindrical shape, in the interior of which the conductor or conductors run. It is also conceivable to surround only one of the conductors with an insulating sleeve and to not or only partially surround the other with an insulating sleeve. Appropriate solutions are known to experts in the field. At the proximal end of the support arms, the conductor is connected to a power source via the proximal section of the resectoscope, as described above.

The counter electrode is spaced apart from the working electrode. This distance is sufficient to electrically isolate the two electrodes from one another. A distance of about 2 mm is usually sufficient for this. The counter electrode can thus be spaced apart 2 mm or more from the working electrode, preferably 3 mm or more, particularly preferably 4 mm or more. The counter electrode is preferably arranged longitudinally, i.e., along the longitudinal axis of the electrode instrument, at the same height or proximal to the working electrode.

The working electrode can cut through tissue when high-frequency current is applied and can be used, for example, to remove a tumor or excess prostate tissue. For this purpose, the electrode instrument, in particular the working electrode, must be moved in a suitable manner while cutting with the high-frequency generator switched on.

The working electrode can have various shapes that are known in the field of high-frequency surgery. It can be configured, for example, as a loop electrode, band electrode or vaporization button. A vaporization button is a partially spherical, usually semi-spherical, working electrode, which is also referred to as PlasmaButton. The working electrode is preferably such a partially spherical vaporization button.

According to the invention, the working electrode and the counter electrode are spatially separated from one another in such a way that the distance between them cannot be bridged by means of a straight, for example rod-shaped, conductor which has a length of 6 mm or less. In other words, the arrangement of the working electrode and the counter electrode prevents a conductive connection between the two electrodes and thus a short circuit from occurring between the two electrodes by touching the two electrodes simultaneously with another conductor. A bridging of the distance between the two electrodes is understood here to mean the establishment of an electrically conductive connection between the two electrodes. This further conductor, which is not part of the electrode instrument or the resectoscope, can be part of an electrically conductive implant, for example. The conductor can therefore also be referred to as a conductor outside the instrument. The conductor outside the instrument is not tissue or liquid, but usually made of an electrically conductive metal or an alloy containing the latter. The conductor outside the instrument is essentially straight and has no major curvatures.

6 mm corresponds to the shortest anchor length of currently used prostate implants. In many cases, however, implants with an anchor length of 8 mm are used. In one embodiment of the invention, the working electrode and the counter electrode are therefore spatially separated from one another in such a way that the distance between them cannot be bridged by means of a straight, for example rod-shaped, conductor which has a length of 8 mm or less.

The counter electrode is arranged in the distal end region of the electrode instrument. This means that the counter electrode is located, for example, in the distal third, preferably in the distal fifth, more preferably in the distal tenth of the electrode instrument, but does not have to be arranged directly at the distal end of the instrument. As a rule, the counter electrode will be arranged relatively close to the working electrode, but electrically insulated from it.

In preferred embodiments, a short circuit through a conductor outside the instrument is prevented in accordance with the invention by the distance between the working electrode and the counter electrode being more than 6 mm. Since the maximum length of the anchors of the smallest common implants is 6 mm, the risk of a short circuit between the working electrode and the counter electrode can be sufficiently reduced in this way. The distance between the working electrode and counter electrode can be more than 6 mm, more than 8 mm, more than 9 mm, more than 10 mm, more than 11 mm, more than 12 mm, more than 13 mm, more than 14 mm, or more than 15 mm. The distance is preferably more than 8 mm, since this corresponds to the length of the anchors of frequently used implants. In other words, the distance between the working electrode and the counter electrode is between 6 mm and 20 mm, between 8 mm and 20 mm, between 10 mm and 20 mm, between 11 mm and 20 mm, between 12 mm and 20 mm, between 13 mm and 20 mm, between 14 mm and 20 mm, or between 15 mm and 20 mm. A maximum distance of 15 mm can also be provided. It is clear that the term "between" excludes the specified lower and upper limit in the indicated ranges. The distances mentioned are longer than the usual distances between the working electrode and the counter electrode, which are generally about 4 mm. According to the invention, the support arm and/or the support arms is/are thus extended accordingly. However, it is also conceivable to arrange the counter electrode further proximally on a support arm of conventional length.

As an alternative or in addition to the distance extension described, according to the invention, a short circuit between the working electrode and the counter electrode can be prevented by placing an insulator between the two electrodes in such a way that no electrically conductive connection can be established between the two electrodes by means of a straight conductor outside the instrument. In other words, in these embodiments, an insulator is arranged spatially between the working electrode and the counter electrode, which intersects all straight connecting lines which are possible between the working electrode and the counter electrode and have a length of 6 mm or less. In preferred embodiments, the insulator intersects all straight connecting lines that are possible between the working electrode and counter electrode and have a length of 8 mm or less. More preferably, the insulator not only intersects all straight connecting lines that are 6 mm or less or 8 mm or less in length, but also all straight connecting lines that are possible between the working electrode and the counter electrode.

All straight lines which run from an outer point of the working electrode to an outer point of the counter electrode are regarded as straight connecting lines. All points on the outer wall of the electrodes count as 'outer points.' Only those straight lines are considered as straight connecting lines which and/or whose route could effectively be used for the electrically conductive connection of the working electrode and counter electrode by means of a straight conductor. Thus, in particular, straight connecting lines are preferably cut through the insulator on which, in principle, a straight conductor could be placed in order to establish an electrical connection between the working electrode and the counter electrode. It is clear that the straight connecting lines in the sense of the invention are virtual, i.e., the do not constitute real technical connecting elements. Straight lines that are cut by one or more other insulating elements of the electrode instrument and on which therefore no electrically conductive connection could be made are not considered to be straight connecting lines. Such other insulating elements can be, for example, the support arm or arms, provided that they are surrounded by an insulating sleeve.

The insulator intersects the straight connecting line, as described above. 'Intersecting' means in the usual sense of the word that the insolator crosses the straight connecting line in its course or intersects it in its course.

The insulator can comprise one or more insulating elements, for example 1, 2, 3, 4, 5, 6 or more. The insulating elements can be directly adjacent to one another in the insolator, or can be arranged at some distance from one another.

Suitable materials from which the insulator can be constructed are known to those skilled in the art. Since the insulator is electrically insulating, essentially all electrically insulating materials can be used, it being preferred to use plasma-resistant materials because of the proximity to the working electrode. The insulator should not be damaged by the working electrode, to which high-frequency current is applied and that is heated. For this purpose, the insulator is preferably completely, at least to an extent that ensures its insulating ability, made of an electrically non-conductive, i.e., electrically insulating, material. Such materials are known to those skilled in the art and include, for example, ceramics and plastics. Suitable plastics can be selected, for example, from the group consisting of fluoropolymers and cycloolefin copolymers.

The insulator may be spaced apart from the two or one of the electrodes. In certain embodiments, however, it is preferred that the insulator is directly adjacent to one or both electrodes, for example is arranged adjacent to both electrodes between the two electrodes. For example, the insulator can directly adjoin the working electrode and/or the counter electrode. It is e.g. conceivable to arrange the insulator on the non-spherical side of a vaporization button, i.e., the side of the working electrode which faces away from the tissue during surgery. The counter electrode can then be arranged proximal to the working electrode or on the side of the insulator which faces away from the working electrode.

For this purpose, the insulator can be configured, for example, in the form of a plate, i.e., have a flat and even shape, which is preferably of the same thickness everywhere in one plane. In this way, the insulator can cross the straight connecting lines in a material-saving and space-saving manner and at the same time take up as little space as possible in the direction of the straight connecting lines.

The insulator can, for example, have a flat cuboid or L-shaped cross section. An insulator with an L-shaped cross section is particularly suitable for shielding the working electrode if it is a vaporization button. The insulator having an L-shaped cross section can then be placed in such a way that the vaporization button is enclosed on two sides by the insulator, one side for fastening the insulator preferably being the side of the working electrode facing the support arm and the other side intersecting the straight connecting lines described elsewhere herein.

If the insulator is alternatively formed with a flat cuboid cross-section, it can, for example, lie adjacent to the working electrode on the side of the working electrode which faces the support arm. In this embodiment, the counter electrode could in turn be arranged directly on the side of the insulator which faces the support arm and faces away from the working electrode. The counter electrode and working electrode will then not protrude radially beyond the insulator, in particular will not protrude beyond the insulator in such a way that straight connecting lines are formed between the working electrode and the counter electrode, via which an electrically conductive connection could be established by means of a straight conductor. In this embodiment, the working electrode and the counter electrode can be placed very close together, so that the current path is short when the electrode is used.

It is also conceivable that the working electrode and the insulator are arranged on one side of the electrode instrument and the counter electrode is arranged on the side of the electrode instrument that is opposite with reference to the longitudinal axis of the electrode instrument. As a result of this spatial separation of the working electrode and the counter electrode, there are no straight connecting lines between the electrodes in the sense of the invention. Since the working electrodes are often arranged on a support arm or arms which are angled in the distal end region, the counter electrode can, for example, be arranged on the side of the support arm that is opposite with reference to the direction of angulation, with reference to the longitudinal axis of the electrode instrument, and in a section of the support arm in which the support arm preferably runs essentially parallel to the longitudinal axis of the electrode instrument.

BRIEF DESCRIPTION OF THE FIGURES

Exemplary embodiments of the invention are shown schematically in the drawings. The figures show.

EMBODIMENTS

Further advantages, characteristics and features of the present invention will become apparent in the following detailed description of exemplary embodiments with reference to the accompanying drawings. However, the invention is not restricted to these exemplary embodiments.

Figure 1:
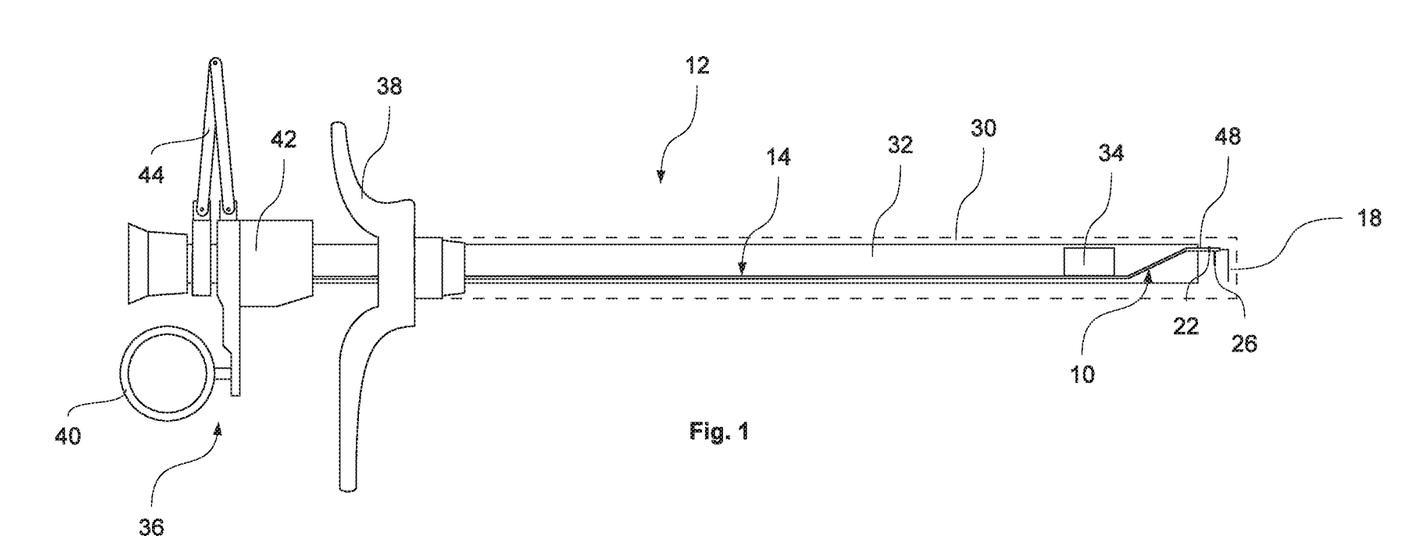
FIG. 1 a schematic side view of a resectoscope according to the invention.
Figure 2:
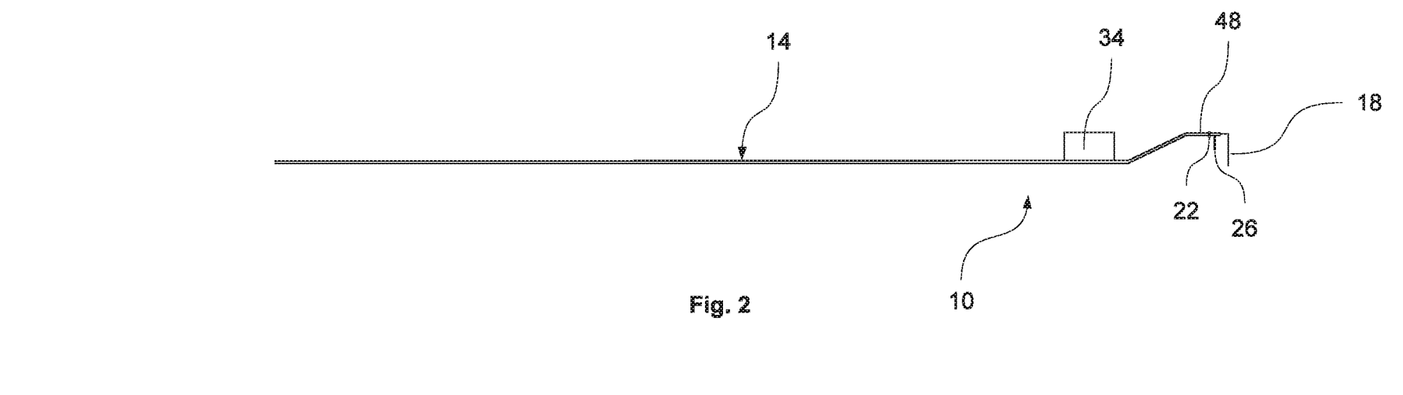
FIG. 2 a schematic side view of an electrode instrument according to the invention.

FIG. 1 shows a schematic side view of a resectoscope 12 according to the invention, FIG. 2 shows the electrode instrument 10 arranged therein. The electrode instrument 10 shown in both figures has a working electrode 18 and a counter electrode 22, as well as an insulator 26, which prevents short circuits caused by external conductors 24.

The resectoscope 12 has a shaft which comprises a cladding tube 30, which is shown in broken lines in FIG. 1. An inner tube 32 runs inside the cladding tube 30 and the electrode instrument 10 runs inside the inner tube 32. In addition, further elements (not shown here) can run inside the cladding tube 30, such as, for example, an optical system, optical fiber bundles and/or irrigation tubes.

The electrode instrument 10 is arranged so as to be longitudinally displaceable inside the inner tube 32 and is protected against transverse displacements, i.e., displacements in the radial direction, by two guide elements 34. The guide elements 34, of which only one is visible in FIGS. 1 and 2, are configured to be complementary to the inner wall of the inner tube 32 as guide plates, which together take on a partially cylindrical shape.

The electrode instrument 10 can be moved axially in the distal and proximal direction by actuation of a handle part 40 in a forcibly guided manner. It can be pushed beyond the distal end of the inner tube 32 and the distal end of the cladding tube 30. This enables the surgeon to manipulate tissue further away from the resectoscope tip. For this purpose, the inner tube 32 and/or electrode instrument 10 are also rotatably mounted about their longitudinal axis.

The electrode instrument 10 has a working electrode 18 at its distal end, which in the embodiment shown is configured as a cutting loop. Tissue can be removed by means of the working electrode 18 by electrosurgical ablation. Here, a high-frequency electrical voltage is applied to the working electrode 18 in order to cut tissue.

The electrode instrument 10 also has a counter electrode 22 in its distal end region and is therefore a bipolar electrode instrument in which two electrodes are connected separately from one another to two poles of a high-frequency generator, not shown here. Current can flow between these electrodes if, for example, they are present together in a liquid, for example the liquid of the bladder. The counter electrode 22 is arranged at a distance, as shown, for example, at a proximal distance from the working electrode 18. Both electrodes are arranged on the support arm and/or arms 48 of the electrode instrument 10.

The support arm or arms 48 of the electrode instrument 10 are rod-shaped. A first electrical conductor 16 and a second electrical conductor 24 (not shown), which form the working electrode or the counter electrode in their distal end regions, run inside the support arm or arms 48. The counter electrode 22 is, for example, electrically conductively connected to the second conductor 20, but not to the first conductor 16, to which there is only an insulating connection. The counter electrode 22 is thus only electrically connected to the second conductor 20 and the working electrode 18 only connected to the first conductor 16.

In the distal end region of the electrode instrument 10 there are therefore two electrodes 18 and 22 which are electrically separated from one another and are connected separately via the conductors 16 and 20. The conductors 16 and 20 are connected to connecting cables with separate poles of a high-frequency generator, not shown. If the high-frequency generator is switched on, there are different voltage poles on the working electrode 18 and the counter electrode 22 and current flows between them through the electrically conductive body fluid.

If such bipolar instruments are used, after attaching conductive implants, for example to the prostate, there is a risk that a piece of an implant touched by both electrodes will lead to a conductive bridging and a short circuit between the working electrode 18 and the counter electrode 22. Therefore, according to the invention, as shown in FIGS. 4 to 7, it is provided to spatially separate the working electrode 18 and the counter electrode 22 from one another in such a way that the distance between them cannot be bridged by means of a straight conductor 24 outside the instrument, which has a length of 6 mm or less.

The resectoscope 12 shown has a passive transporter, in which the carriage 42 is displaced in the distal direction against the distal, first handle part 38 by a relative movement of the handle parts 38, 40 arranged proximally from the resectoscope shaft on the handle 36 against a spring force applied by a spring bridge 44. When the carriage 42 is displaced in the distal direction against the handle part 38, the electrode instrument 10 is displaced in a positively guided manner in the distal direction in a manner not shown. When the handle parts 38, 40 are relieved, the spring force generated by the spring bridge 44 forces the carriage 42 back into its rest position, the shaft of the resectoscope 12 and thus also the electrode instrument 10 being pulled in the proximal direction. When the carriage 42 is moved back, an electrosurgical intervention with the electrode instrument 10 can be carried out without manual force from the surgeon, that is to say passively.

Figure 3:
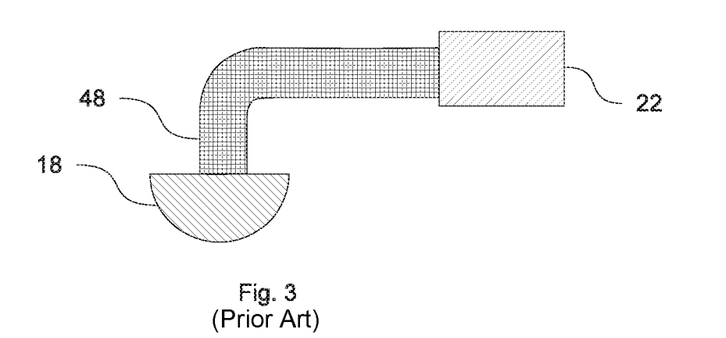
FIG. 3 a schematic side view of the distal end region of an electrode instrument from the prior art, the electrode instrument having a vaporization button working electrode.

FIG. 3 shows a schematic side view of the distal end region of an electrode instrument 10 from the prior art, the electrode instrument 10 having a working electrode 18 which is configured as a vaporization button (PlasmaButton). The working electrode 18 is arranged at the distal end of a support arm 48, the support arm 48 running inside a distal section, inside which the working electrode 18 is arranged transversely to the longitudinal axis of the electrode instrument 10 and merging in a proximally angled manner into a section of the distal end region which is arranged parallel to the longitudinal axis of the electrode instrument 10. In this section, which is aligned parallel to the longitudinal axis, the counter electrode 22 is arranged, which is attached to the outer shell of the support arm 48. The minimum distance between the working electrode 18 and the counter electrode 22 is 6 mm or less, so that there is a risk that a short circuit between the counter electrode 22 and the working electrode 18 is caused by conductive implant parts. Moreover, the support arm 48 is electrically insulated, i.e., outside of the working electrode 18 and counter electrode 22. In an alternative embodiment, the vaporization button can be held by two support arms 48. In this way, the first conductor 16 can be guided in one support arm 48 and the second conductor 24 can be guided in the other support arm 48.

Figure 4:
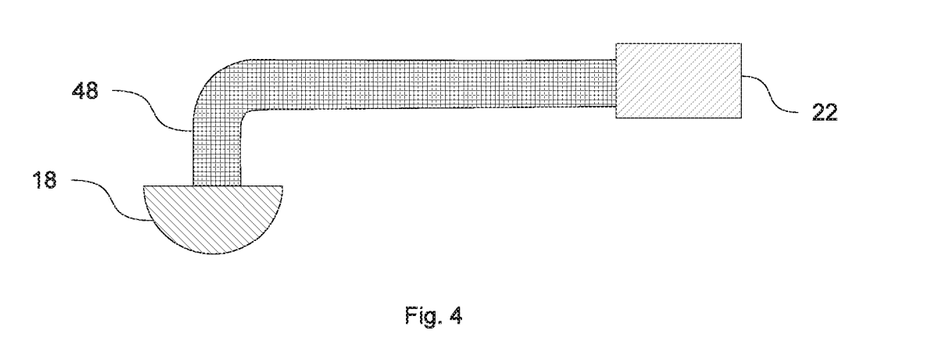
FIG. 4 a schematic side view of the distal end region of an electrode instrument according to the invention, the electrode instrument having a vaporization button working electrode and the distal end region of the support arm being extended compared to the prior art.

FIG. 4 shows a schematic side view of the distal end region of an electrode instrument 10 according to the invention, the electrode instrument 10 having a working electrode 18 which is configured as a vaporization button. The distal end region of the support arm 48 is extended compared to the prior art shown in FIG. 3, so that the distance between the working electrode 18 and the counter electrode 22 is more than 6 mm. As a result, there is advantageously no longer a risk of a potential short circuit due to touching implant parts, since the implant parts with which the resectoscope can come into contact are generally no longer than 6 mm. As an alternative to an extension of the support arm 48, it is also conceivable to extend the distance between the working electrode 18 and the counter electrode 22 in another way, for example by a more proximal arrangement of the counter electrode 22 at the support arm.

Figure 5:
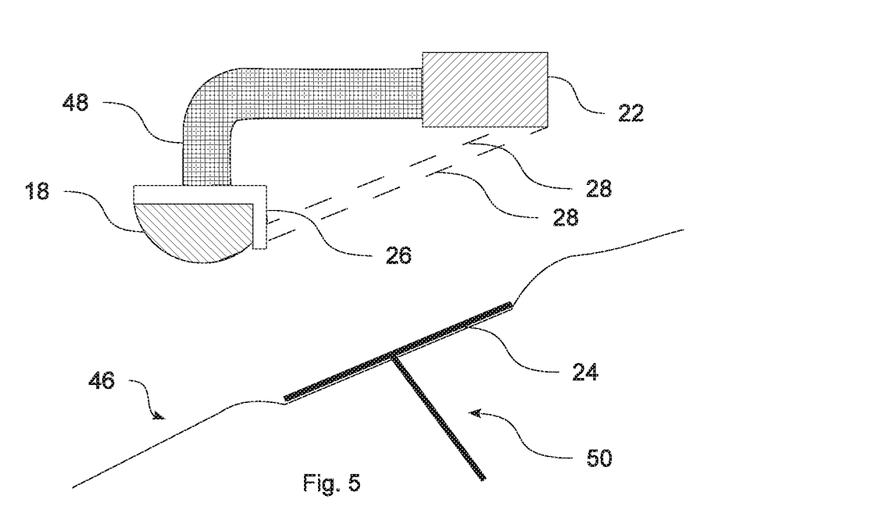
FIG. 5 a schematic side view of the distal end region of an electrode instrument according to the invention, the electrode instrument having a vaporization button working electrode and an insulator with an L-shaped cross section, which intersects the straight lines between the working electrode and the counter electrode.

FIG. 5 shows a schematic side view of the distal end region of an electrode instrument 10 according to the invention, the electrode instrument 10 having a working electrode 18 which is configured as a vaporization button. The electrode instrument 10 also has an insulator 26, which has an L-shaped cross section. The insulator 26 intersects all the virtual straight connecting lines 28 between the working electrode 18 and the counter electrode 22 on which it would otherwise be possible to establish an electrically conductive connection by means of a straight external conductor 24. Such a conductor 24, which is an anchor part of an implant 50, is also shown by way of example. The implant 50 is anchored in the tissue 46. Only one side of the implant 50 is shown, which is T-shaped at both ends. Tissue 46 may be, for example, prostate tissue that is compressed to keep the ureter open.

It can be seen that by means of the anchor-like straight end of the implant 50, the conductor 24, no electrically conductive connection can be produced by simultaneously touching the working electrode 18 and the counter electrode 22, since the insulator 26 prevents this. The insulator 26 is arranged on the one hand with one side adjacent to the back of the button electrode facing away from the tissue and on the other hand with a second section, which is formed by its L-shaped cross section, arranged proximally to the side of the working electrode 18. This second section of the L-shaped insulator 26 separates all straight connecting lines 28 that can potentially be bridged by means of a straight conductor 24.

Figure 6:
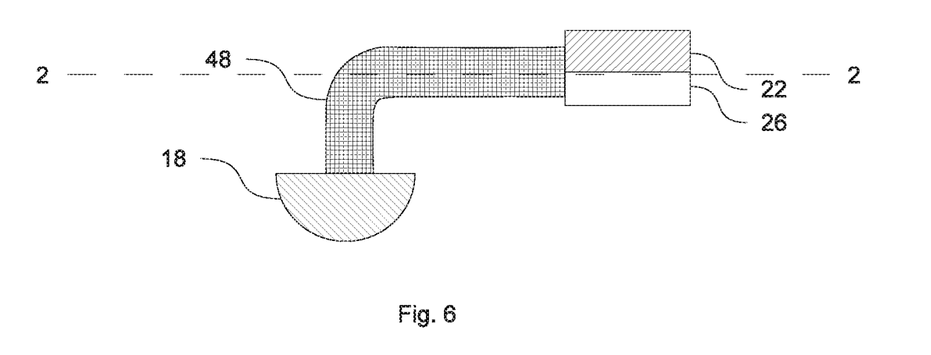
FIG. 6 a schematic side view of the distal end region of an electrode instrument according to the invention, the electrode instrument having a vaporization button working electrode and an insulator on one side of the electrode instrument and a counter electrode on the side of the electrode instrument that is opposite with reference to the longitudinal axis of the electrode instrument.

FIG. 6 shows a schematic side view of the distal end region of an electrode instrument 10 according to the invention, the electrode instrument 10 having a working electrode 18 and an insulator 26 on one side of the electrode instrument 10 and a counter electrode 22 on the side of the electrode instrument 10 that is opposite with reference to the longitudinal axis 2-2 of the electrode instrument 10. The position of the counter electrode 22 in the distal end region of the electrode instrument 10, i.e., the distance of the counter electrode 22 to the distal end and the proximal end of the electrode instrument 10, is comparable or identical to its position in electrode instruments 10 in prior art, such as that shown in FIG. 3. In contrast to these conventional instruments, however, the counter electrode 22 does not comprise any parts which are arranged on the same side of the electrode instrument 10 as the working electrode 18. Instead, an insulator is arranged on this side of the electrode instrument 10 at the level of the counter electrode 22. This can, for example, be semicylindrical around the support arm 48 and/or in one piece with the usual insulating sleeve of the support arm 48. In preferred embodiments, the insulator 26 is formed by an electrically insulating coating on one side of the support arm 48, for example by a coating on the underside, which is arranged on the same side of the electrode instrument 10 as the working electrode 18. The counter electrode 22 is formed on the opposite side on the outer wall of the support arm 48. Since the support arm 48 and the insulator 26 are arranged between the counter electrode 22 and the working electrode 18 and the insulator 26 intersects all straight connecting lines 28 which can be used for potential electrical bridging, there is no risk of a short circuit between the working electrode 18 and the counter electrode 22.

Figure 7:
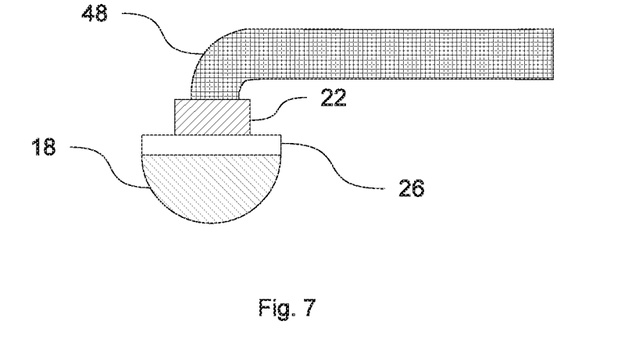
FIG. 7 a schematic side view of the distal end region of an electrode instrument according to the invention, the electrode instrument having a vaporization button working electrode and an insulator having a rectangular cross section, which is arranged adjacent between the working electrode and the counter electrode.

FIG. 7 shows a schematic side view of the distal end region of an electrode instrument 10 according to the invention, the electrode instrument 10 having a working electrode 18 which is configured as a vaporization button. The support arm 48 of the electrode instrument 10, which carries the working electrode 18 at its distal end, merges in an angled manner in its distal end region into a section which is arranged approximately transversely to the longitudinal axis of the electrode instrument 10 (angled section). In addition to the working electrode 18, the insulator 26 and the counter electrode 22 are also arranged in this angled section. Working electrode 18 and counter electrode 22 are not spatially far apart. The two electrodes are nevertheless reliably electrically insulated from one another by the insulator 26 arranged between the electrodes. All three elements are arranged essentially equicentrically around the at least one support arm 48, i.e., the central axis (longitudinal axis) of the support arm 48 preferably also represents the central axis of the insulator 26 and the counter electrode 22, preferably also the working electrode 18. Furthermore, the width of the three elements ensures that no electrical connection can be made between working electrode 18 and counter electrode 22 by means of an external, straight conductor 24. For this purpose, at least one of the two electrodes is generally narrower on all sides than the insulator 26 arranged between the electrodes. In the example shown, this is the counter electrode 22. The insulator 26 has a substantially cylindrical shape. It is clear that the insulator 26 has corresponding openings for the conductor 16 leading to the working electrode 18.

Although the present invention has been described in detail with reference to the exemplary embodiments, it is obvious to the person skilled in the art that the invention is not restricted to these exemplary embodiments, but rather that modifications are possible in such a way that individual features may be omitted or other combinations of the individual features presented may be realized, provided the scope of protection of the appended claims is not exceeded. The present disclosure includes all combinations of the individual features presented.

| Reference list | |
|---|---|
| 10 | Electrode instrument |
| 12 | Resectoscope |
| 14 | Shaft section |
| 16 | First conductor |
| 18 | Working electrode |
| 20 | Second conductor |
| 22 | Counter electrode |
| 24 | Conductor |
| 26 | Insulator |

-continued

| Reference list | |
|---|---|
| 28 | Straight connecting lines |
| 30 | Cladding tube |
| 32 | Inner tube |
| 34 | Support elements |
| 36 | Handle |
| 38 | Handle part |
| 40 | Handle part |
| 42 | Carriage |
| 44 | Spring bridge |
| 46 | Tissue |
| 48 | Support arm |
| 50 | Implant |

The invention claimed is:

1. A bipolar electrode instrument for use in a resectoscope, the electrode instrument including:
   a first conductor that extends through an elongated shaft section and being configured to form a working electrode at a distal-most end of the electrode instrument, the working electrode configured to receive a high-frequency current;
   a second conductor extending through the shaft section and forming a counter electrode at a distal end region of the electrode instrument such that the counter electrode is provided proximally of the working electrode, wherein:
      the working electrode and the counter electrode are spatially separated such that a distance between the working electrode and the counter electrode cannot be bridged by a straight conductor having a length of 6 mm or less;
   an insulator arranged spatially between the working electrode and the counter electrode, the insulator intersecting all possible straight connecting lines between the working electrode and the counter electrode that are 6 mm or less in length; and
   a support arm configured to carry the working electrode, wherein:
      a central axis of the working electrode is coincident with a central axis of the support arm and intersects with a central axis of the counter electrode.

2. The electrode instrument according to claim 1, wherein the distance between the working electrode and the counter electrode is more than 6 mm.

3. The electrode instrument according to claim 1, wherein the insulator is adjacent to the working electrode.

4. The electrode instrument according to claim 1, wherein the insulator is adjacent to the counter electrode.

5. The electrode instrument according to claim 1, wherein the insulator is plate-shaped.

6. The electrode instrument according to claim 1, wherein the working electrode and the insulator are arranged on one side of the electrode instrument and the counter electrode is arranged on the side of a side of the electrode instrument that is opposite with reference to a longitudinal axis of the electrode instrument.

7. The electrode instrument according to claim 1, wherein the working electrode is a partially spherical vaporization electrode.

8. A resectoscope for endoscopic surgery with a cladding tube, wherein an electrode instrument according to claim 1 is mounted so as to be longitudinally displaceable inside the cladding tube.

9. The electrode instrument according to claim 2, wherein the distance between the working electrode and the counter electrode is more than 8 mm.

10. The electrode instrument according to claim 1, wherein the support arm is an L-shaped support arm.

11. A bipolar electrode instrument for use in a resectoscope, the electrode instrument including:
   a first conductor that extends through an elongated shaft section and being configured to form a working electrode at a distal-most end of the electrode instrument, the working electrode configured to receive a high-frequency current;
   a second conductor extending through the shaft section and forming a counter electrode at a distal end region of the electrode instrument such that the counter electrode is provided proximally of the working electrode, wherein:
      the working electrode and the counter electrode are spatially separated such that a distance between the working electrode and the counter electrode cannot be bridged by a straight conductor having a length of 6 mm or less; and
   an insulator arranged spatially between the working electrode and the counter electrode, the insulator intersecting all possible straight connecting lines between the working electrode and the counter electrode that are 6 mm or less in length; and
   a support arm configured to carry the working electrode, the support arm being L-shaped, wherein the working electrode, counter electrode, and insulator are arranged concentrically about the support arm.

* * * * *